(12) United States Patent
Gerard et al.

(10) Patent No.: US 6,850,635 B2
(45) Date of Patent: Feb. 1, 2005

(54) METHOD AND SYSTEM FOR EXTRACTING SPINE FRONTAL GEOMETRICAL DATA INCLUDING VERTEBRA PEDICLE LOCATIONS

(75) Inventors: Olivier Gerard, Paris (FR); Milena Planells-Rodriguez, Toulouse Cedex (FR); Pierre Lelong, Nogent sur Marne (FR); Sherif Makram-Ebeid, Dampierre (FR)

(73) Assignee: Koninklijke Philips Electronics, N.V., Eindhoven (NL)

( * ) Notice: Subject to any disclaimer, the term of this patent is extended or adjusted under 35 U.S.C. 154(b) by 677 days.

(21) Appl. No.: 09/965,414

(22) Filed: Sep. 27, 2001

(65) Prior Publication Data

US 2002/0061126 A1 May 23, 2002

(30) Foreign Application Priority Data

Sep. 29, 2000 (EP) .......................................... 00402698

(51) Int. Cl.⁷ ................................................ G06K 9/00
(52) U.S. Cl. ........................ 382/132; 382/190; 128/922
(58) Field of Search ................................ 382/100, 128, 382/131, 132, 173, 190, 195, 278; 128/922; 250/455.11; 378/46, 90, 92

(56) References Cited

U.S. PATENT DOCUMENTS

| | | | |
|---|---|---|---|
| 5,841,833 A | 11/1998 | Mazess et al. ............. | 378/98.9 |
| 6,608,916 B1 * | 8/2003 | Wei et al. .................... | 382/132 |
| 6,608,917 B1 * | 8/2003 | Wei et al. .................... | 382/132 |
| 6,724,924 B1 * | 4/2004 | Wei et al. .................... | 382/132 |
| 2002/0136437 A1 * | 9/2002 | Gerard et al. .............. | 382/128 |

FOREIGN PATENT DOCUMENTS

| | | | |
|---|---|---|---|
| WO | WO9952068 | 10/1999 | ............. G06T/5/00 |

OTHER PUBLICATIONS

"Digitat Radiography Segmentation of Scotiotic Vertebrae Body using Deformabte Models" by □□Claude Kauffmann and Jacques A. de Guise in SPIE Vot. 3:34, pp. 243–251.*
Kim et al. ("Automatic Scoliosis Detection Based on Local Centroids Evaluation on Moire Topographic Images of Human Backs", IEEE, pp. 1314–1320, 2001).*
Novosad et al. (Three–Dimensional(3–D) Reconstruction of the Spine From a Single X–ray Image and prior Vertebra Models, IEEE, pp. 1628–1639, 2004).*
Noone et al. ("Development and Corrective Biomechanics for Scoliosis", IEEE, pp. 37–41, 1991).*

(List continued on next page.)

*Primary Examiner*—Samir Ahmed
*Assistant Examiner*—Anand Bhatnagar
(74) *Attorney, Agent, or Firm*—John Vodopia

(57) ABSTRACT

The invention relates to an image processing method of extracting geometrical data of the spine, for extracting the left and right pedicle landmarks of each spine vertebra, comprising steps of:

acquiring image data of a 2-D frontal image of the spine; associating spine States to vertebra positions along the spine and estimating locations of left and right pedicle landmark Candidates in each State; defining a State Cost for forming Couples of left and right pedicle landmark Candidates ($P_L$ and $P_R$); estimating sets of Best Couple Candidates, in each State, from the lowest State Costs; defining a Path Cost to go from one State to the next State; selecting a pedicle landmark Couple in each spine State (V) among the Best Couple Candidates from the minimum Path Costs, and localizing the left and right pedicle landmarks of each spine vertebra from said selected pedicle landmark Couple.

The invention also relates to a system, a medical apparatus and a program product for carrying out the method.
Application: Medical Imaging x-ray Medical System and apparatus; Program Product for Medical Imaging.

11 Claims, 5 Drawing Sheets

OTHER PUBLICATIONS

Lin ("The Simplified Spine Modeling By 3-D Bezier Curve Based on the Orthogonal Spinal Radiographic Images," IEEE, pp. 944-946, 2003).*

"Digital Radiography Segmentation of Scoliotic Vertebral Body using Deformable Models" by Claude Kauffmann and Jacques A. de Guise in SPIE vol. 3034, pp. 243-251.

* cited by examiner

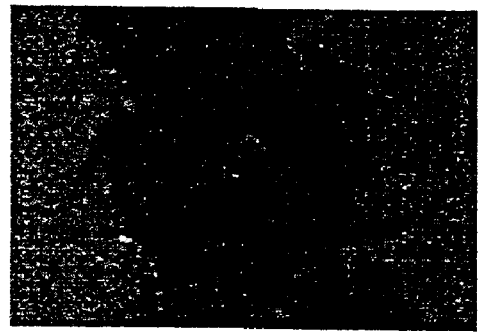
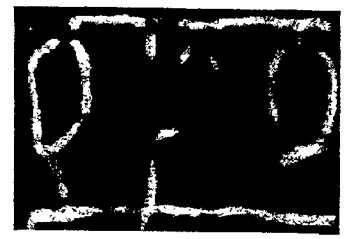
FIG.5A  FIG.5B
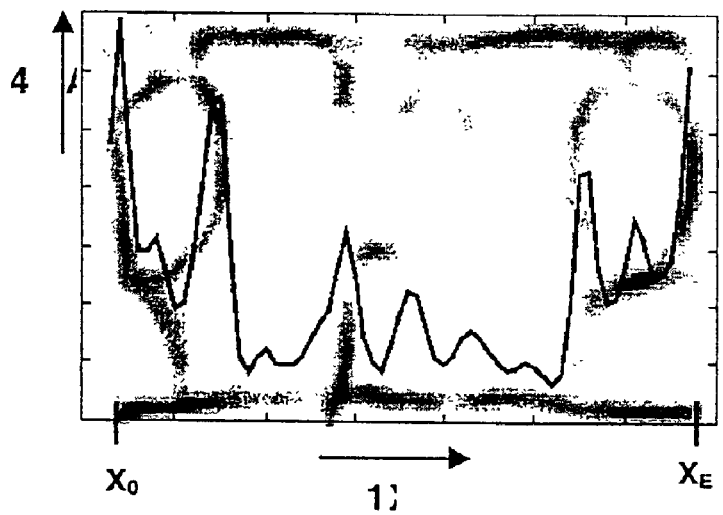
FIG.6A
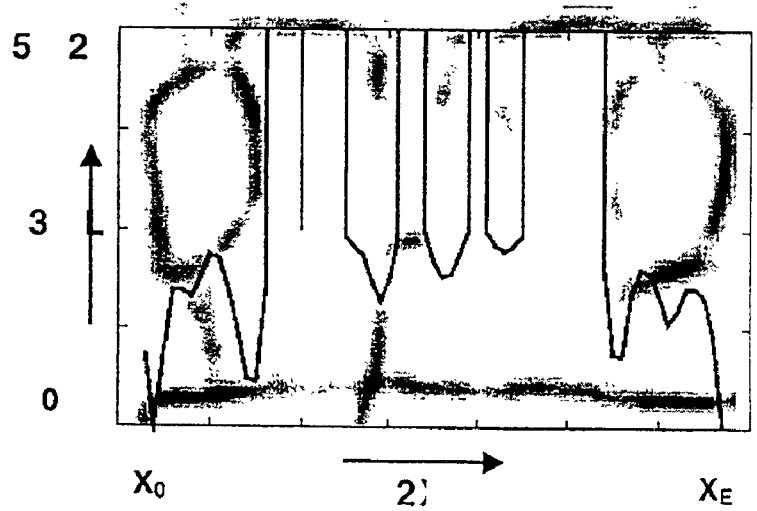
FIG.6B

METHOD AND SYSTEM FOR EXTRACTING SPINE FRONTAL GEOMETRICAL DATA INCLUDING VERTEBRA PEDICLE LOCATIONS

FIELD OF THE INVENTION

The invention relates to an image processing method for extracting frontal geometrical data of a spine image including vertebra pedicle locations. The invention finds its application in medical imaging.

BACKGROUND OF THE INVENTION

A segmentation method applied to the spine is already known of the publication "Digital Radiography Segmentation of Scoliotic Vertebral Body using Deformable Models" by Claude Kauffmann and Jacques A. de Guise in SPIE Vol. 3034, pp. 243–251. This publication describes a computer segmentation method based on the active contour model (g-snake) and using a prior knowledge. This method is adapted and used to detect automatically the contour lines of each vertebral body independently in digital radiographs of the scoliotic spine. These contour lines are used to identify correspondent anatomical landmarks for the 3D reconstruction of the scoliotic spine using a bi-planar technique. The steps comprise: constructing a standard template for each kind of vertebrae (thoracic or lumbar), performing three best fits of the appropriate template on the spine radiograph, g-snake energy minimization, selection of a best contour for each vertebra individually, and anatomical landmark extraction (including corners and spine center-line points). Previous steps of digitization of the spine centerline and acquisition of a prior knowledge including the height and width of the standard template are first performed.

SUMMARY OF THE INVENTION

The method known of the cited document does not describe steps for specifically extracting the landmark corresponding to the location of the spine pedicles. It only provides the corner locations. Now, the pedicle locations are particularly useful to estimate the rotation angle of every vertebrae.

The present invention has for object to propose a image processing method to extract spine data called landmarks corresponding to the pedicle locations. This method has steps to perform the extraction of these pedicle landmarks using previously determined locations of other landmarks corresponding to the vertebra corner projections. For example, these steps are carried out by processing a frontal image of a number of adjacent vertebrae of the spine. Such an image processing method is claimed in claim 1. An imaging system, an X-ray apparatus and a computer program product are also claimed to carry out the method.

These extracted geometrical data permit of providing information appropriate to help diagnosing scoliosis even on a single 2-D image. Said data also permit of three-dimensional image reconstruction of the spine from two bi-planar images using a technique of geometric modeling. Three-dimensional images of the spine particularly help diagnosing scoliosis because said disease is a 3-D deformity of the spine. The construction of the 3-D model of the spine is based on the location of the corner landmarks and the pedicle landmarks of the spine vertebrae.

BRIEF DESCRIPTION OF THE DRAWINGS

The invention is described hereafter in detail in reference to diagrammatic figures, wherein:

FIG. 5A represents a particular vertebra and FIG. 5B represents the corresponding icon;

FIG. 6A shows, superimposed on an icon, a curve of feature accumulation and FIG. 6B shows the corresponding curve of Costs;

DESCRIPTION OF EMBODIMENTS

The invention relates to an image processing method for extracting geometrical data of the spine, in order to localize specific elements of the spine in spine images, for studying spine deformities. The specific elements are the pedicles of the vertebrae.

Figure 1A:
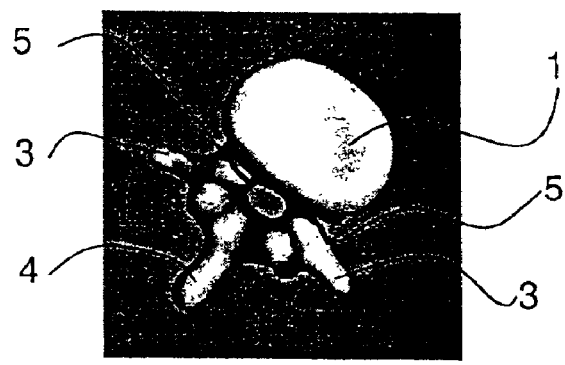
FIG. 1A, FIG. 1B, FIG. 1C are representations of a vertebra in various perspectives.
Figure 1B:
Figure 1C:

Referring to FIG. 1A to FIG. 1C, in perspective views, a vertebra shows a body 7, which defines the spine axis and the shape of the vertebral discs and which is substantially cylindrical with flattened elliptic bases 1, 2 called endplates (FIG. 1A, FIG. 1C); a spineous process 4 located in the plane of symmetry of the vertebra (FIG. 1A, FIG. 1B); two transverse processes 3 (FIG. 1A, FIG. 1C) and two pedicles 5 located at the bases of the vertebral arches (FIG. 1A, FIG. 1B); the pedicles define the intrinsic rotation of the vertebra around its axis.

Figures 2A, 2B:
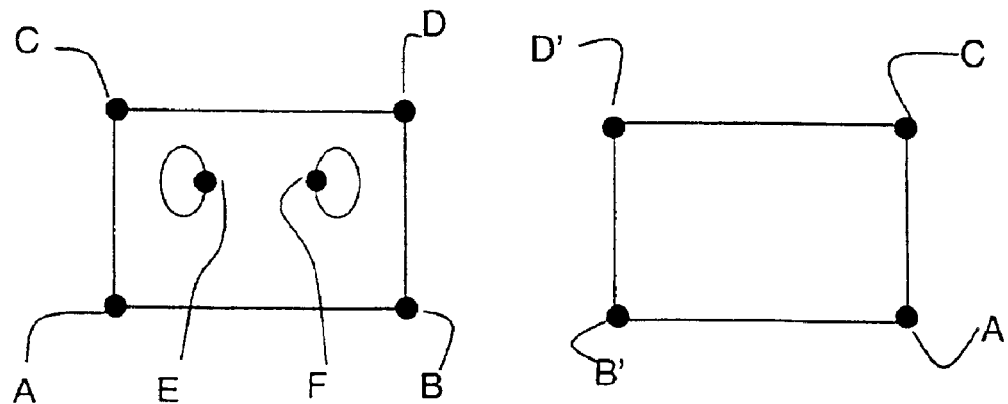
FIG. 2A and FIG. 2B show optimal landmarks of a vertebra, in frontal and lateral views.
Figures 4A, 4B:
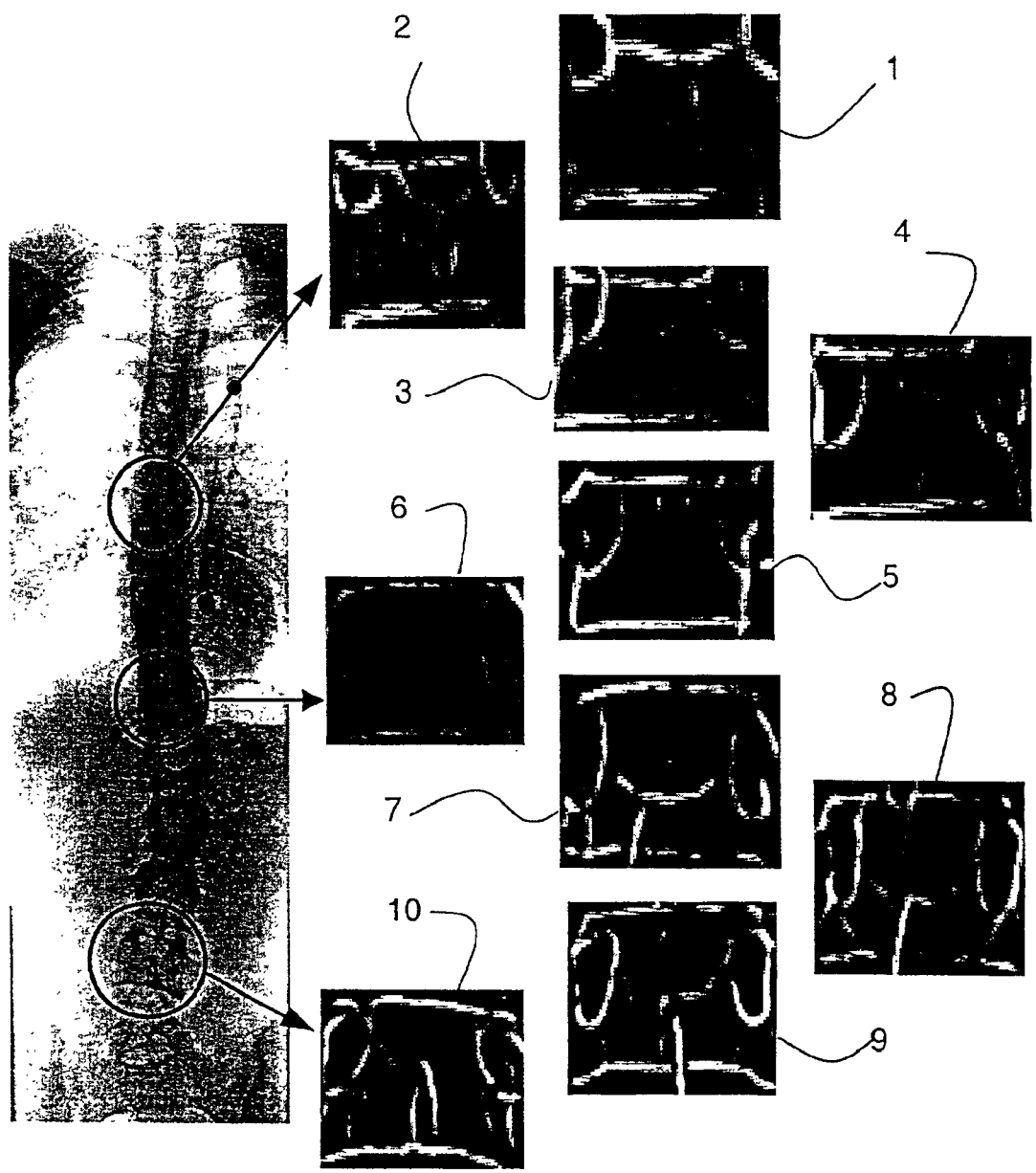
FIG. 4A shows a spine frontal view and FIG. 4B shows icons of successive vertebrae, each icon representing the features of the vertebra in its local referential.

Six optimal landmarks are selected, as represented respectively in the frontal and in the lateral images shown in FIG. 2A and FIG. 2B. These landmarks are the extremities of the projection of the vertebra body, which are the corners A, B, C, D, A', B', C', D' of the vertebra; and the position of the inner points E, F of the projection of the pedicles, further on called pedicle landmarks. The present method supposes that the corners A, B, C, D of the interesting vertebrae have already been located in a frontal view. This method comprises steps of:

A frontal image of an examined patient is acquired. This image may be formed by X-ray imaging, as shown in FIG. 4A. Each point has a luminance intensity and coordinates in a cartesian referential whose axes are parallel to the sides of said frontal view. The frontal view may comprise a number of adjacent vertebrae, for example sixteen (16) vertebrae. The processing method encounters problems due to the position of the pedicles with respect to the other landmarks in the different vertebrae along the spine. In the thoracic vertebrae, the pedicles are almost at the same height as the upper endplate or even higher and they are very difficult to detect. In the lumbar vertebrae the pedicles are in the upper half of the vertebrae and they are easier to detect. The vertebrae have individual axes of rotation that are generally not vertical and that are different from each other.

Each vertebra is processed separately in order to take advantage of the local intensity properties for pedicle detection. In the region of the processed vertebra, the sides of the vertebra present a high contrast, which would interfere in the detection of the pedicles. In order to prevent this interfering, a restricted Region of Scanning is defined, which is a part of the image to be processed for pedicle detection. To this end, each vertebra is attributed an independent cartesian referential in which the Region of Scanning is further defined.

Figure 3A:
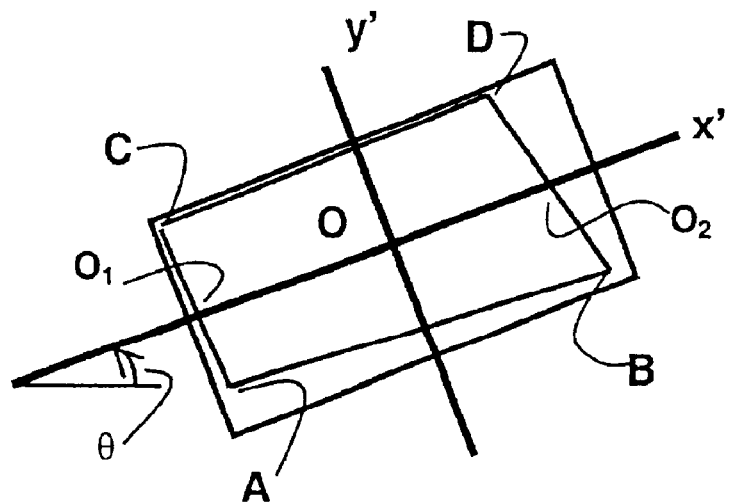
FIG. 3A and FIG. 3B illustrate the step of positioning of the vertebra in a local referential.

Referring to FIG. 3A, the current frontal original vertebra image shows the corner landmarks A, B, C, D. The middle points of the left and right lines joining the corners, respectively CA, DB, are denoted $O_1$ for AC and $O_2$ for BD. The coordinates of these middle points $O_1$, $O_2$ are computed in the referential of the frontal view. The line $O_1O_2$ that goes through these points is an axis X' that is generally not horizontal as above-described. The orthogonal axis Y' going through the center O of $O_1O_2$, is generally not vertical. A new referential X, Y is determined with a horizontal axis X and a vertical axis Y. The Region of Scanning is obtained by rotating a part of the of the current frontal original vertebra image using a rotation angle $\theta$ that is the angle between the X'-axis and the current horizontal axis defined in the frontal view. The new X-axis is parallel to this current axis. The center of the rotation is O and the part of the image to rotate is determined by the largest projections of the corners A, B, C and D onto the new X-axis.

Figure 3B:
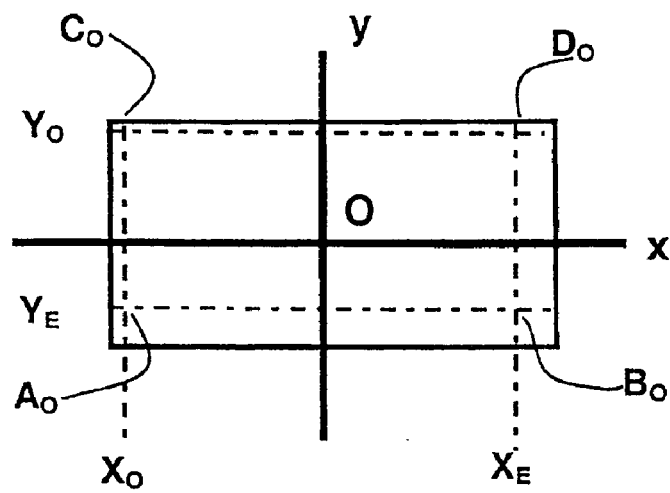

Referring to FIG. 3B, the part of the image resulting from said rotation is rectangular with O as the center and constitutes the Region of Scanning. It is delimited by horizontal lines parallel to the X-axis at the ordinates $Y_0$, $Y_E$, and by vertical lines parallel to the Y-axis at the abscissae $X_0$, $X_E$. So, the Region of Scanning in this new referential X, Y is defined by the rightmost projection of corners A and C onto the X-axis leading to $X_0$, the leftmost projection of corners B and D onto the same X-axis leading to $X_E$. The same procedure for the Y-axis leads to $Y_0$ and $Y_E$. The Region of Scanning is defined by New Corners that are $A_0(X_0, Y_E)$, $B_0(X_E, Y_E)$, $D_0(X_E, Y_E)$, and $C_0(X_0, Y_0)$.

Features that are characteristic of the points found in said Region of Scanning are estimated. The results of this operation of Feature Estimation permits of constructing an Image of Features in the local referential X, Y of the Region of Scanning. Different features can be considered for pedicle detection, such as gradient values, gray levels or intensity variance. The features that are considered as most effective to discriminate the thin structures representing the pedicles are ridgeness values.

The image of the Region of Scanning can be a positive image, which is considered as a 3-D picture, having two dimensions for the co-ordinates of pixels and a third dimension for the intensity signals associated to said pixels. A ridge is a crest-like structure formed by adjacent pixels having intensity signals that are maximum in a neighborhood, said pixels having specific dispositions the ones with respect to the others resulting in specific gradient values with respect to orientations. A ridge pixel shows a low intensity gradient in a first determined direction in its neighborhood, and shows an intensity gradient that is maximum in a direction perpendicular to said first direction. The more a given structure is formed of pixels verifying this gradient property, the more the ridgeness measure of the structure is high. Instead of ridges, troughs can be considered in a negative original image of the Region of Scanning for instance obtained by X-ray imaging. In an X-ray negative image, a ridge structure is a dark structure on a lighter background. In this case, the calculations for extracting the pedicles have for an object to extract trough pixels, which can be determined by measures similar to ridgeness calculations. In ridgeness calculations applied to troughs determination, the estimation of specific intensity gradients that is required for characterizing ridges is still valuable for characterizing troughs. So, in the description of the present method, these calculations are called "ridgeness" calculations, whether they are applied to ridges or troughs in the Region of Scanning.

FIG. 5A shows an original frontal image of a vertebra. The method comprises a step of "ridgeness" calculation applied to the image of the Region of Scanning corresponding to the vertebra of FIG. 5A. This "ridgeness" calculation is performed by applying, on the pixels, filters known as ridge-filters, which determine the pixels of the ridge or trough structures. Based on this ridgeness calculation, each pixel of the Region of Scanning is further associated to a ridgeness data. The resulting image is called Feature Image as shown on FIG. 5B.

Preferably, in a variant of this step of Feature Image formation, the features are computed on a Region of Interest ROI, which is constituted of a number of adjacent vertebrae and of a border region around these vertebrae represented in a frontal view such as the view shown on FIG. 4A. From this Feature computation in the ROI, an image called ROI Feature Image is formed. The calculation of various new referentials by rotation and the calculation of various limited Regions of Scanning in said new referentials, as above-described, are then further performed based on said ROI Feature Image. FIG. 4B shows various icons of Feature Images corresponding to said various Regions of Scanning. The icon 2 of FIG. 4B is a Feature Image corresponding the circled vertebra of FIG. 4A. The icon 1 is a Feature Image of a vertebra above the circled one and the icons 3 to 10 are Feature Images of the successive vertebrae below this circled one.

For every vertebra, the contrast of the Feature Image, in each icon corresponding to the Region of Scanning, is preferably further linearly enhanced. This Feature Image is scanned parallel to the vertical Y-axis, and the Feature values are accumulated by summing, in the direction of the Y-axis for every X coordinates between $X_0$ and $X_E$, called X-Region. Actually, this accumulation may be limited to be computed only on the upper-region of the vertebral body. This upper-region may be defined as covering only 70% of the length of the Y-axes of the Region of Scanning, since the pedicles are usually located on this upper-region. Avoiding to scan the lowest part of the Region of Scanning enables to avoid taking into account the lower endplates, thus avoiding interfering disturbances, and enables to reduce calculation amount.

Referring to FIG. 6A, the summed Feature Values are projected onto the horizontal X-axis. This operation results in a curve of the Accumulated Feature Values, called AS, showing maximum values called Peaks corresponding to the occurrence of ridges substantially parallel to the vertical Y-axis. The curve S is superimposed onto the Feature Image inverted in intensity.

These Accumulated Values are further transformed into Local Costs. In this step of Local Cost calculation, an inversion operation is required for providing a correspondence between the highest Accumulated Values or Peaks of the curve AS and lowest Local Costs. The X-region is split into two parts: a left part and a right part. For both parts independently, the Accumulated Values are submitted to a threshold operation. As an example, a threshold is set at 80% of the average level of the Accumulated Values. So, LC being the associated Local Cost:

LC=0 when associated to the highest Accumulated values;
LC=1000 when associated to an Accumulated Value equal to the predetermined threshold level;
LC is infinite when associated to every location on the X-axis where an Accumulated Value is found to be below the predetermined threshold level.

For the other locations, an associated cost LC is computed as the inverse of the corresponding Accumulated Value: a precise equation being for example:

$$LC = 1000 * \left(1 - \frac{AS - fAS}{M_S}\right)$$

where f the threshold level, S is the Accumulated Value, AS is its average and $M_S$ its maximum value. FIG. 6A shows the accumulation curve and FIG. 6B shows the local cost curves for the vertebra presented in FIGS. 5A, 5B. In FIG. 6B, for visualization purpose, the image of the vertebra features are included, with reversed contrast, on the background of the graphs, as in FIG. 6A. It is to be noted that the cost graph has been limited to a 0–2000 range but actually goes to an INFINITE COST, which is defined at $10^9$, with 1000 limiting the useful region.

Projected pedicles mostly look like thin vertical lines. The pedicle landmarks of FIG. 2A situated on said thin lines are detected in the frontal view. As shown on FIG. 2A, pedicle projections are elliptical-shaped. The left and right external borders of the elliptical-shaped pedicles may be a source of errors. According to the present method, the Y-accumulation procedure is used to perform a discrimination between the left and the right borders of each elliptical shaped pedicle. The Feature Images may include some other sources of errors that are the borders of the vertebra, which also show high feature response and which are vertical, and the projection of the spurious process, which may appear as a vertical line roughly in the middle of the vertebral body but mostly in the lowest part of the body. According to the present method, the effects of these possible errors will be reduced by a further Dynamic Programming procedure.

It is important to note that only the internal border locations of the pedicles are looked for, because only these locations are used to estimate the rotation of the vertebra for diagnosing the severity of spine scoliosis. The pedicle landmarks that are on the internal border locations of the left and right pedicles are respectively called Left and Right Pedicle Locations. As explained previously, the present method has for an object to simultaneously detect the Left and Right Pedicle Locations for the specific spine vertebra of a specific patient. For performing this operation, the couples of Left and Right Pedicle Locations, which are represented by couples of corresponding abscissae $X_L$, $X_R$ on the X-axis, are looked for, for all vertebrae. Since a Local Cost is associated to each abscissa on the X-axis, couples $X_L$, $X_R$ showing the lowest Costs are looked for, for each vertebra. For each given Left Pedicle Location $X_L$, several Right Pedicle Locations $X_R$ are possible, thus forming several couple candidates of Left and Right Pedicle Locations. For estimating the best couple candidates:

the whole Region of Interest ROI of the spine is considered in order to take into account the locations of each couple candidate of a given vertebra with respect to the other couple candidate of the other vertebrae, which give more robustness in the location determinations;

the location of each vertebra in the spine, called state, is defined by a vertebra index V, which is the name or the position of said vertebra in the spine, and a Database is accessible to provide average values of the distance, hereafter called Pedicle Distance, separating candidate couples of Left and Right Pedicle Locations, for each given vertebra;

every possible Left Pedicle Location is determined in a range of coordinates between $X_0$ and the middle of the X-Region (middle of $X_0 X_E$), and a certain number of position candidates for the Right Pedicle Location is determined, typically in ten (10) bands called "bins", gathering 1 to 3 Right Pedicle Location candidates;

The procedure of finding Right Pedicle Locations $P_R$, called $P_R$ candidate, from a given particular Left Pedicle Location $P_L$, called $P_L$ candidate, comprises:

searching for $P_R$ candidates at a distance $\overline{D_{L,R}}$ estimated from the database, within a range proportional to the standard deviation to this distance, thus defining a search region;

dividing this search region into a number of bins, favorably ten (10) bins, of equal size;

selecting the same number (10) of $P_R$ candidates, one for each bin. If one bin is found empty, an infinite cost is applied. If several $P_R$ candidates are inside the same bin, the $P_R$ candidate having the minimum local cost is selected. Thus for every $P_L$ candidate, a set of said number of for example ten (10) $P_R$ candidates is built.

computing the local cost associated with one state, defined by the vertebra index V, with the $P_L$ candidate and with an associated $P_R$ candidate, as the sum of three terms that are:

the Cost associated to the $P_L$ candidate;

the minimum of the Costs associated to every $P_R$ candidate in the current bin, the deviation of the current distance $D_{L,R}$ between said $P_L$ and $P_R$ candidates with respect to the "average" distances $\overline{D_{L,R}}$ as estimated from the database. Actually the distance term is normalized by the cosine of the rotational angle of the current vertebra estimated by using information from only the left location.

Figure 7A:
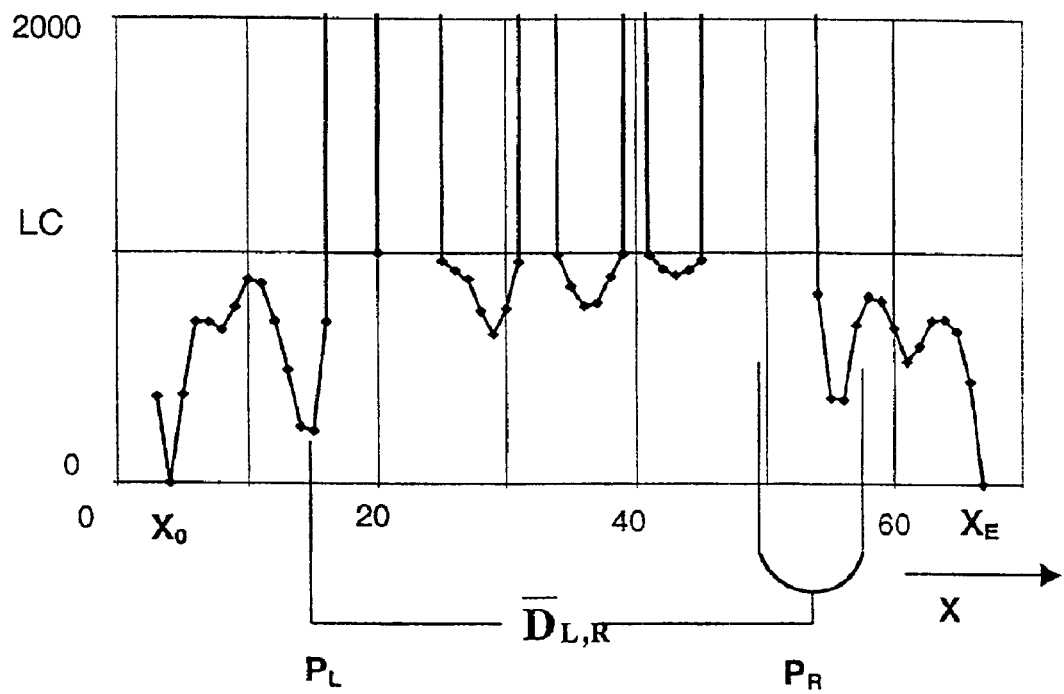
FIG. 7A is the curve of Costs for the determination of a couple of pedicles and FIG. 7B is a 3-D Cost Matrix for determining the best paths where the left and right pedicles are to be found along the spine.

Referring to FIG. 7A, the actual computation is performed according to:

$$SC(L,R) = LC_L + LC_R + (D_{L,R} - \overline{D_{L,R}})$$

which is the State Cost SC(L, R) for associating possible $P_L$ and $P_R$ candidates, expressed as the Sum of the Local Costs $LC_L$ and $LC_R$ at the indicated locations of said possible candidates, plus the difference between the actual distance $D_{L,R}$ between the locations of said candidates and the corresponding "average" normalized distance $\overline{D_{L,R}}$ for the given vertebra. It is to be noted that these Local Cost computations are performed for every vertebra and thus the previous equation depends upon V, the vertebra index. These State Costs SC(V, L, R) are used for defining the Matrix-Costs of the 3D-state-Matrix illustrated on FIG. 7B.

A Dynamic Programming (DP) procedure is carried out in order to determine one Best Couple among the $P_L$ and $P_R$ candidates, for each vertebra of the spine, taking into account that for two successive vertebrae, the pedicles are substantially aligned (except in the case of a vertebral displacement) and that for the whole spine, the paths on which the pedicles are disposed are substantially smooth. This Dynamic Programming (DP) is a non-iterative method, effective in contour detection, that uses Energy Functions and that is not described hereafter, because it is well known of those skilled in the art. This procedure has for a purpose to determine the "most likely path" for the location of the $P_L$ and $P_R$ candidates. The points that are to be linked are those that are most likely part of the pedicle internal sides. The Dynamic Programming (DP) procedure calculates the Path of lowest Cost going from a node to another to yield this Path. The DP is performed in the frontal view in the vertical direction.

Figure 7B:
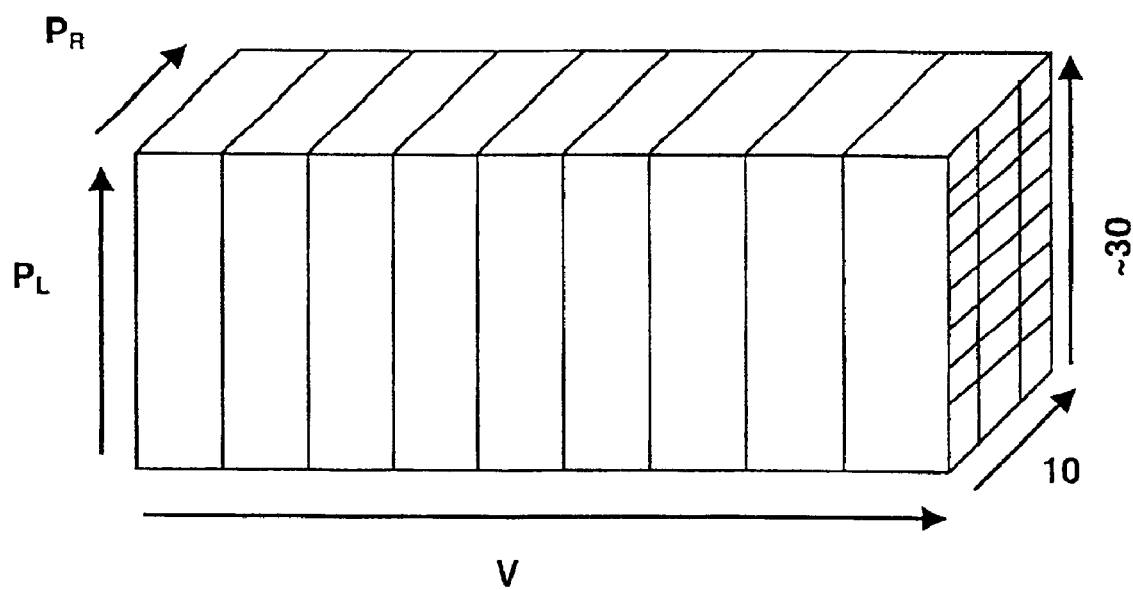

A 3-D Matrix of States is defined, as depicted in FIG. 7B. This Matrix has a $P_L$-axis (vertical), for the number, for example 30, of $P_L$ candidates; it has a $P_R$-axis (in the depth direction of FIG. 7B) for the number of $P_R$ bins (10 bins) per each $P_L$ candidate; the $P_L$-axis and the $P_R$-axis define a plane, regarded as a band (vertical band on FIG. 7B) of the 3-D Matrix. The third dimension (horizontal) of this Matrix is the State given by the index V of the current vertebra under study among the number N of adjacent vertebrae that is user specified, typically 5 or 16 vertebrae.

For carrying out the Dynamic Programming Procedure, a first pass, called Forward Pass, is performed in a forward direction along the V-axis. In a first State (for a first vertebra), a first couple of $P_L$ and $P_R$ candidates, for instance denoted by $P_{L1}$, $P_{R1}$, is defined as the one with the lowest State Cost in the corresponding first band of the Matrix of States. The procedure has for an object to determine, in the following State (for the second vertebra), a couple of $P_L$ and $P_R$ candidates, for example denoted by $P_{L2}$, $P_{R2}$, which is one with the optimum State Cost in this second State and which is linked to the first couple of the first State with the lowest Transition Cost. This Transition Cost is favorably the Sum of the distances between $P_{L1}$, $P_{L2}$ and between $P_{R1}$, $P_{R2}$. This couple $P_{L2}$, $P_{R2}$ that fulfils the Cost conditions in the second State is called Best Predecessor. So, for each State, the Best Predecessor is defined as the one with the lowest Path Cost. The search for this Best Predecessor is actually performed by first looking for the $P_L$ candidate that is the closest to the one of the current State (±10 locations). Then, for determining the best $P_R$ candidate in said current State, a Path Cost is defined for linking the current State and its Predecessor State, composed of three Costs:

the Local Costs of the previous State,
the State Cost of the current State,
the Transition Cost that is the Sum of the Distances between the couples of $P_L$ and $P_R$ candidates and is intended to penalize sudden local variation of the rotational angle.

A second pass, called Backward Pass, is performed in the backward direction. The Backward Pass determines, for every State, the most probable predecessor, i.e. the Couple of the previous State that has the minimal Path Cost. The Backward Pass begins in the State of the last vertebra having the lowest Path Cost. Going backwards, the Dynamic Programming Procedure retrieves the locations for both pedicles for every vertebra. Thus, it defines a line in the 3-D Cost Matrix. Two vertical lines are then drawn in the local referentials to display the determined pedicle landmark locations for every linked vertebra.

The user can then select and move faulty lines towards correct locations. As soon as he releases a line, the cost is modified such that a zero (0) Cost is associated to the selected location and an infinite Cost is set for all the other locations in the current half vertebra. The building of a new Cost Matrix is then performed, followed by a new Dynamic Programming Procedure.

Figure 8:
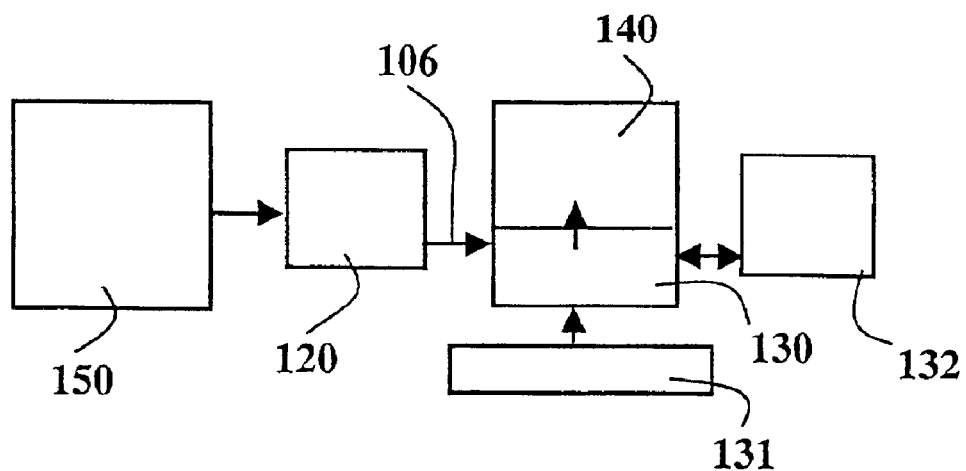
FIG. 8 is a functional block diagram of medical diagnostic imaging system and apparatus for carrying out the method.

Referring to FIG. 8, a medical examination apparatus 150 comprises means for acquiring digital frontal image data of the spine, and a digital processing system 120 for processing these data according to the processing method above-described. The medical examination apparatus comprises means for providing image data to the processing system 120 which has at least one output 106 to provide image data to display and/or storage means 130, 140. The display and storage means may respectively be the screen 140 and the memory of a workstation 110. Said storage means may be alternately external storage means. This image processing system 120 may be a suitably programmed computer of the workstation 130, or a special purpose processor having circuit means such as LUTs, Memories, Filters, Logic Operators, that are arranged to perform the functions of the method steps according to the invention. The workstation 130 may also comprise a keyboard 131 and a mouse 132.

What is claimed is:

1. An image processing method of extracting geometrical data of the spine, for extracting the left and right pedicle landmarks of each spine vertebra, comprising steps of:

acquiring image data of a 2-D frontal image of the spine; associating spine States to vertebra positions along the spine and estimating locations of left and right pedicle landmark Candidates ($P_L$ and $P_R$) in each State (V);

defining a State Cost for forming Couples of left and right pedicle landmark Candidates;

estimating sets of Best Couple Candidates, in each State, from the lowest State Costs;

defining a Path Cost to go from one State to the next State;

selecting a pedicle landmark Couple in each spine State among the Best Couple Candidates from the minimum Path Costs, and localizing the left and right pedicle landmarks of each spine vertebra from said selected pedicle landmark Couple.

2. The image processing method of claim 1, wherein the step of selecting said pedicle landmark Couple comprises:

defining a 3-D Cost Matrix having planes, defining Bands corresponding to the States, in which the Best Couple Candidates are located, said Cost Matrix having a directional axis, orthogonal to said planes, for indices corresponding to spine States;

performing a first pass in a first direction along said directional axis, for computing the Path Costs between the Best Couple Candidates of each State and the Best Couple Candidates of the corresponding Predecessor State, and performing a second pass in the reverse direction for selecting a Couple in each State that show the lowest Path Cost to go to the next State.

3. The image processing method of claim 2, wherein the Path Cost definition comprises compounding Local Costs related to the landmark location Candidates in the predecessor State, the State Cost for forming Couple Candidates in the current State and a Transition Cost that is function of the Distance between the Couple Candidates in each State, which penalizes sudden local variation of the rotational angle of the vertebrae of the predecessor and current State.

4. The image processing method of claim 3, wherein the State Cost definition comprises summing respective Local Costs for left and right pedicle landmark location Candidates, and a normalized Distance between said left and right pedicle landmark candidate locations in each State, which takes the index of the State into account.

5. The image processing method of claim 1, wherein the estimation of left and right pedicle landmark location Candidates in each State comprises:

computing, from the spine image data, Features Values that are characteristic of thin structures;

scanning a region, called Region of Scanning, containing the pedicles, for each vertebra, along scan lines substantially parallel to the pedicle internal border lines, where the pedicle landmarks are to be localized; and accumulating Feature Values of each scan line on an axis, called X-axis that is orthogonal to the scan lines, and transforming the accumulated Feature Values into Costs, called Local Costs, measured along said X-axis, said Local Cost Values being the smallest for the highest Accumulated Values;

performing a search for the left and right pedicle landmark location Candidates among the points of said X-axis associated to the smallest Local Costs.

6. The image processing method of claim 5, wherein the determination of the Best Couple Candidates, at a given State, comprises:

determining a range for the left pedicle landmark location Candidates on the X-axis;

determining a number of location Candidates for the right pedicle landmarks, in a Search Region determined on said X-axis at a predetermined Distance of the current left pedicle location Candidate;

dividing said Search Region into a number of bins, each containing a number of right pedicle landmark location Candidates; computing the State Cost and selecting sets of Best Couple Candidates linked by the smallest State Costs.

7. The image processing method of claim 5, wherein the determination of the Region of Scanning comprises:

selecting an image of a current vertebra delimited by lines joining its corner landmarks;

estimating the median axis of the vertebra sides and the angle between said axis and a reference horizontal axis of the 2-D spine frontal image;

rotating the image of said current vertebra by said angle and defining an horizontal axis, which is the X-axis corresponding to said current vertebra; and limiting the rotated image by the leftmost and the rightmost projections of the vertebra corner landmarks on said X-axis, thus defining a rectangular image region used as Region of Scanning.

8. The image processing method of claim 5, wherein the Feature Values are the ridgeness values estimated in the Region of Scanning.

9. A system comprising a suitably programmed computer or a special purpose processor having circuit means, which are arranged to process image data according to the method as claimed in claim 1.

10. A medical examination imaging apparatus having means for acquiring medical digital image data and having a system having access to said medical digital image data according to claim 9, and having display means for displaying the medical digital images and the processed medical digital images.

11. A computer program product comprising a set of instructions for carrying out a method as claimed in claim 1.

* * * * *